United States Patent [19]
Heinen, Jr.

[11] Patent Number: 5,372,131
[45] Date of Patent: Dec. 13, 1994

[54] TRIANGULAR INTRATRACHEAL TUBE

[76] Inventor: Leo F. Heinen, Jr., 301 S. 3rd, Eunice, La. 70535

[21] Appl. No.: 875,741

[22] Filed: Apr. 28, 1992

[51] Int. Cl.⁵ ............................................ A61M 16/00
[52] U.S. Cl. ........................... 128/207.15; 128/207.14; 128/200.26
[58] Field of Search ...................... 128/207.14, 207.15, 128/200.26

[56] References Cited

U.S. PATENT DOCUMENTS 4,156,428  5/1979  Henkin ............................ 128/207.15
4,637,389  1/1987  Heyden ........................... 128/207.15
4,966,141  10/1990  Bacaner et al. ................. 128/207.14
5,060,647  10/1991  Alessi .............................. 128/207.14

Primary Examiner—David A. Wiecking
Assistant Examiner—Aaron J. Lewis

[57] ABSTRACT

An improved intratracheal tube for ventilating the lungs of a patient is disclosed. The tube is generally triangular in crossection to facilitate insertion of the tube through the glottis of the patient. In addition, the tube has at least one lumen which is located anterior of the ventilation lumen in the tube.

5 Claims, 3 Drawing Sheets 5,372,131

TRIANGULAR INTRATRACHEAL TUBE

FIELD OF THE INVENTION

The present invention relates to an improved intratracheal tube which is primarily used to ventilate the lungs of a patient. More particularly, the present invention relates to an intratracheal tube which has an accessory lumen positioned in a substantially anterior position relative to the ventilation lumen.

Background of the Prior Art

Intratracheal tubes are inserted in the trachea of a patient to establish an airway for respiratory support of the patient. The trachea is defined as the thin-walled tube of cartilaginous and membraneous tissue which descends from the larynx to the bronchi for the purpose of carrying air to the lungs. At the upper part of the larynx is a space between the vocal cords called the glottis. The glottis is substantially triangular in shape and is covered by an elastic cartilage termed the epiglottis. The epiglottis effectively prevents foreign matter from entering the trachea and lower lung field.

Intratracheal tubes have been developed for installation through the glottis. These intratracheal tubes include a ventilation lumen having an end which terminates inferior to the glottis and superior to the carina. The intratracheal tube further includes an inflatable cuff which makes a leak resistent seal between the outside diameter of the ventilation tube and the inside diameter of the tracheal tube. The cuff is a thin-wall pliable balloon which is inflatable through a pilot line to seal the lower airway from the upper airway. Because of this closure, the lungs can be selectively inflated with a gas such as air which is forced through the ventilation tube to artifically ventilate the lungs.

The installation of devices such as intratracheal tubes can cause several problems for the patient. For example, the patient may lose his ability to effectively cough and swallow. When the tube dislodges the epiglottis from its usual position, the tube obstructs air from flowing through the trachea. This creates a need for an alternative route to remove secretions from the area around the cuff. Foreign substances such as oral secretions will enter the trachea and will collect outside the ventilation lumen in the region above the inflated cuff. As the fluid pressure above the cuff increases the possibility of fluid seepage around the cuff also increases. If this seepage continues to occur, the patient will probably contact nosocomial pneumonia. If the pressure of the cuff is increased above the standard 25 mm Hg in an effort to reduce fluid seepage, this increased cuff pressure will promote the possibility of tracheal necrosis. If the cuff pressure is reduced below 25 mm Hg, tracheal capillary perfusion will occur and the possibility of fluid seepage will increase.

To prevent the accumulation of fluids above the cuff which leads to the problems stated above, suction catheters and Yaunker suction devices are utilized. To insert a catheter, the operator must haphazardly probe until the catheter is inserted through the glottis to the anterior edge of the inflated cuff. This is accomplished by turning ninety degrees in the oro-pharynx, then blindly threading the catheter through the glottis. This process is extremely difficult and creates significant trauma for the patient. Because of the large number of nerve endings, spontaneous gag reflexes such as bronchospasm, cardiac arrhythmias, and increased cranial pressures can occur. All of these problems create a high degree of patient trauma.

Various devices have been developed to remove fluids from the region above the cuff in a manner which reduces trauma to the patient. For example, U.S. Pat. No. 4,584,998 to McGrail shows that lumens can be built into the walls of a generally circular catheter. In U.S. Pat. No. 4,637,389 to Heyden, a catheter can be inserted through a channel after the endotrachael tube is inserted. This approach initially reduces the size of the apparatus that must be inserted into the tracheal tube. A variation on the circular crossectional shape of the tube is illustrated in U.S. Pat. No. 4,840,173 to Porter, which shows a suction tube merged with a ventilation tube which is generally shaped as an oval in crossection. The oval shape is specifically designed to facilitate the insertion of the endotracheal tube into the tracheal tube and to reduce the trauma to the patient.

Presently available endotracheal tubes remove fluids from above the cuff but do not adequately prevent the installation problems previously discussed. In addition, available tubes restrict the volume of air carried by the lumen. A need, therefore, exists for an improved intratracheal tube which can remove fluids from the trachea and which minimizes the physical trauma to the patient.

SUMMARY OF THE INVENTION

The present invention overcomes the disadvantages of the prior art by furnishing an intratracheal tube which includes a ventilation lumen for installation to a selected position above the carina, an inflatable cuff for sealing the annulus between the ventilation lumen and the trachea, and a lumen substantially located on the anterior side of the ventilation lumen at the position where the intratracheal tube is proximate to the glottis. The method of the invention is practiced by inserting an intratracheal tube, having a lumen on the anterior side of the ventilation lumen, into the trachea, and by further inflating a cuff to reduce fluid flow through the trachea.

DESCRIPTION OF THE PREFERRED EMBODIMENTS

Figure 1:
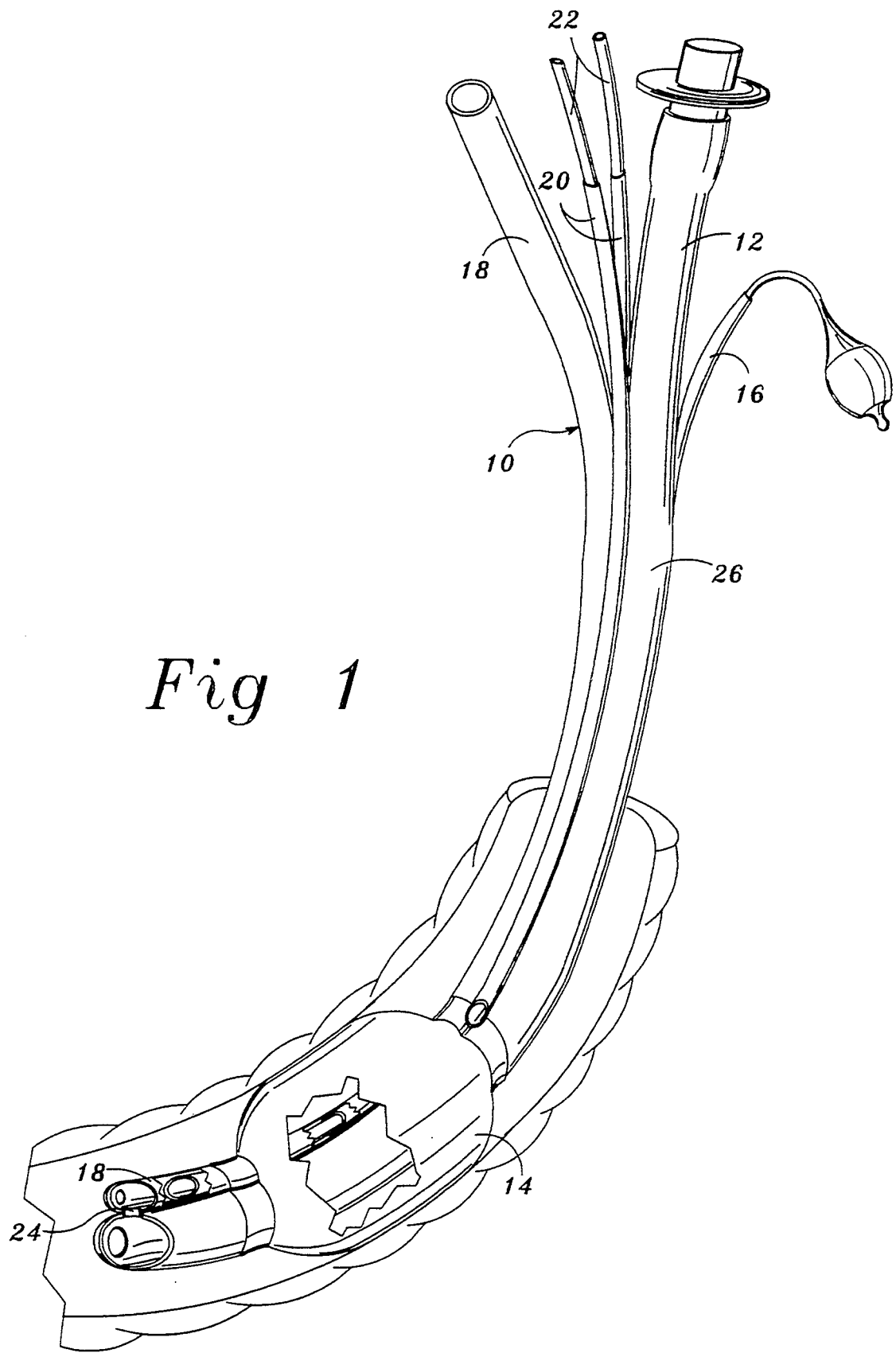
FIG. 1 illustrates an elevation view of the present invention.

The present invention furnishes an improved intratracheal tube which is capable of removing fluids from the trachea while reducing trauma to the patient. The invention enhances the maximum size of the lumens while reducing trauma to the patient and reducing the possibility of secondary infection. As illustrated in FIG. 1, intratracheal tube 10 includes ventilation lumen 12, cuff 14 which can be installed by any known technique such as by inflation with cuff supply tube 16, lumen 18 which has a first end at the ambience and a second end below cuff 14, and lumen 20 which has a first end at the ambience and a second end which is located above cuff In addition, catheters 22 can be installed through lumens 18 and 20 in an alternative embodiment as will be more fully described below.

Figure 2:
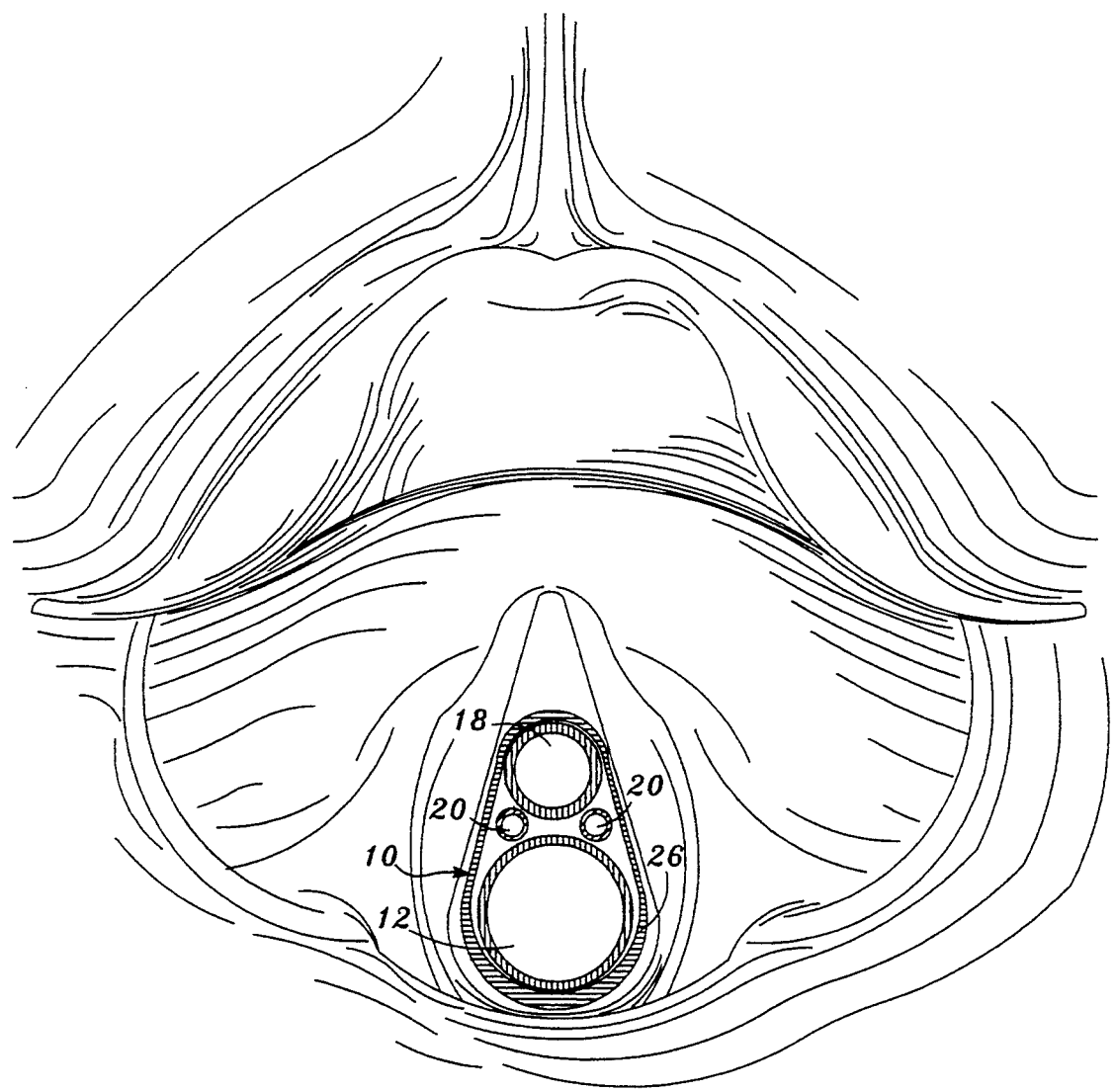
FIG. 2 illustrates a crossectional view of the invention in a position relative to the glottis.
Figure 3:
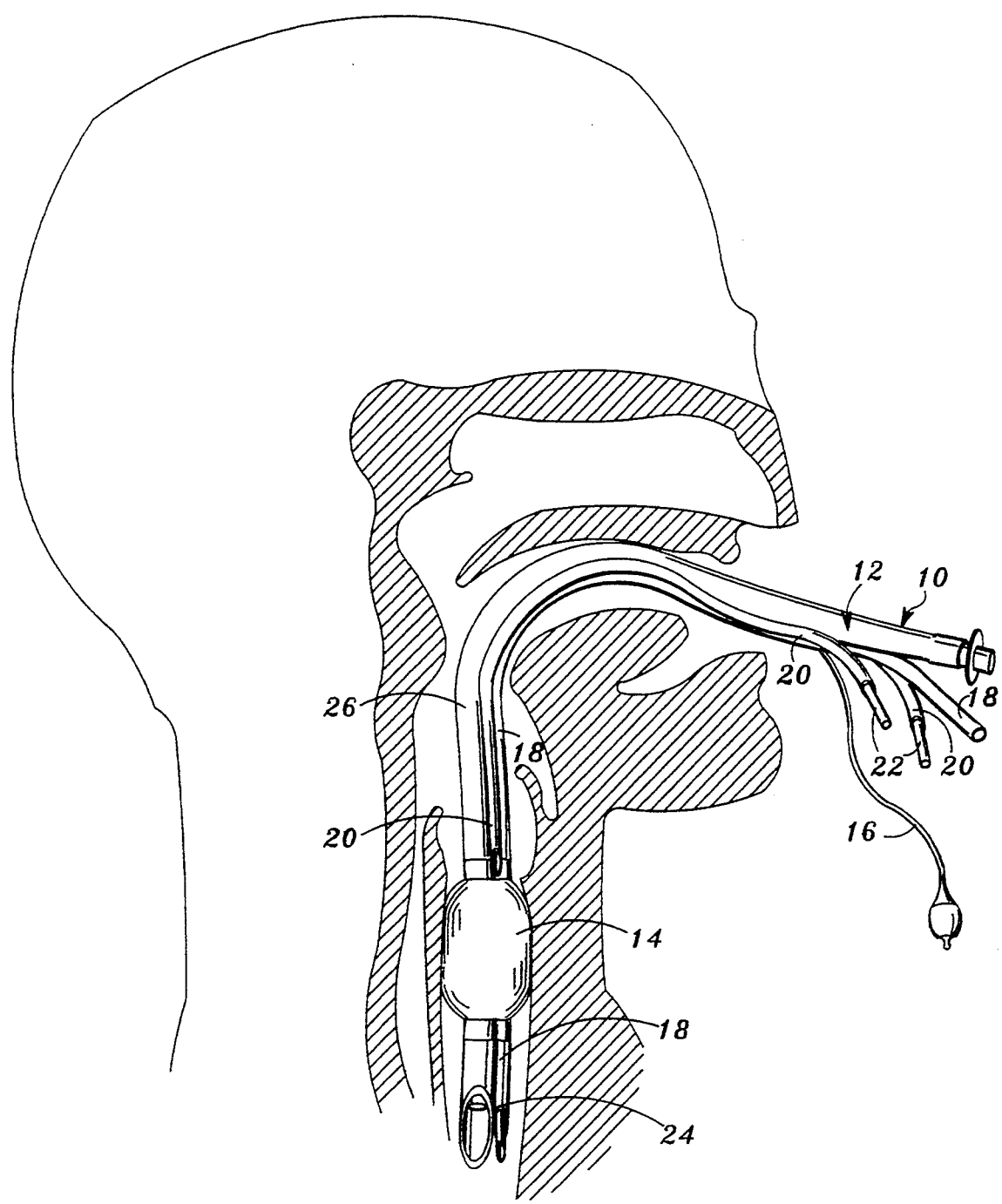
FIG. 3 illustrates the present invention as installed in the trachea of a patient.

It will be noted that tube 10 is generally curved to more closely approximate the curvature of the patient's mouth and tracheal tube. Referring to FIG. 2, it has been discovered that the crossectional area of the glottis is generally triangular in shape, and that the apex of the triangle is generally located toward the face of the patient. For this reason, lumens 18 and 20 are located proximate to lumen 12 so that lumens 18 and 20 are located on the anterior side of lumen 12. This improvement significantly reduces the trauma to the patient and provides good control of the airways near the cuff area, since lumens 18 and 20 are positioned to best utilize the anatomy of the patient's respiratory system. This improvement also recognizes that the glottis is the most restrictive part of the trachea, and therefore comprises the most critical region for the insertion of tube 10. "Anterior" is defined herein as located toward the front of the patient's body, in contrast with an opposite, posterior position. It should also be noted that in one embodiment that lumens 18 and 20 do not need to be located in the anterior position along the entire length of tube 10, but that the critical area is in the region proximate to the glottis. In one embodiment of the invention, lumens 18 and 20 are located in the anterior position substantially along tube 10 to facilitate the insertion of tube 10 into the trachea without requiring the rotation of tube 10 during the insertion process.

Referring to FIG. 1, slots or open channel grooves 24 are located in the second end of lumen 18 to facilitate the entry of fluid into the interior of lumen 18. Referring to FIG. 2, sheath 26 can be utilized to substantially encapsulate all or part of lumens 12, 18 and 20. In another embodiment of the invention, tube 10 can comprise an integrated member which has apertures therethrough which are functionally equivalent to lumens 12, 18 and 20. It is contemplated that lumens 18 and 20 can be used to remove fluids from the trachea or to inject fluids into the trachea. For example, it is Known that antibiotic fluids can be injected into the trachea above the cuff to reduce the threat of infection in such region, particularly before cuff 14 is deflated to remove tube 10 from the trachea. In one embodiment of the invention, a different lumen (not shown) could be installed in tube 10 to have an end terminating above cuff 14 for injecting a fluid above cuff 14 while lumen 20 simultaneously removes fluids from above cuff 14. It is also contemplated by the present invention that lumens 12, 18 and 20 can be sufficiently stiff to serve as injection or suction passageways, or in the alternative that such lumens could be constructed of a flexible material which is compressible upon insertion of tube 10 into the trachea. In this embodiment, catheters 22 could be inserted through the lumens as desired to furnish rigidity to tube 10. As also noted in FIG. 2, the crossectional area defined by the exterior of tube 10 is generally shaped as a triangle to more accurately conform to the anatomical shape of the glottis. In one embodiment of the invention, the corners of the triangular crossection can be rounded to minimize the irritation of the glottis and trachea.

To practice the method of the invention, The intratracheal tube 10 is inserted through the glottis until the distal end of tube 10 is located in the desired position above the carina. Three-way stop cock suction controls (not shown) can be installed on all lumens to selectively open and close the lumens. As previously noted, tube 10 is positioned so that lumens 18 and 20 are located on the anterior side of ventilation lumen 12. Next, cuff 14 is inflated to close the annulus between the exterior surface of tube 10 and the interior wall of the trachea. In other embodiments of the invention, ventilation lumen 12 can be used to move a gas in or out of the lungs, and lumens 18 and 20 can be selectively used to inject fluids into the trachea, or to remove fluids from the trachea. This removal can be automatically performed at selected intervals. In other embodiments, detachable equipment such as tubes (not shown) can be connected to the first ends of lumens 18 and 20 to provide disconnects from tube 10. When tube 10 is removed from the trachea, cuff 14 is deflated and tube 10 can be carefully removed. In a preferred embodiment of the invention, any fluid which has accumulated in the trachea above cuff 14 is removed before cuff 14 is deflated. This step prevents the undesirable fluids from entering the lower airways or the lungs.

It will be appreciated that many modifications and variations to the foregoing description may be made without departing from the scope of the inventive concepts disclosed herein. The embodiments shown herein are merely illustrative and should not be construed as limiting the scope of the invention. As previously, the invention reduces stress and trauma to the patient, reduces the possibility of infection, and is easy to install within the trachea.

What is claimed is:

1. An intratracheal tube for ventilating lungs through a glottis and through the trachea between the vocal cords and the carina, wherein the glottis has a crossectional shape which is substantially shaped as an isosceles triangle having an apex on the anterior, ventral side, comprising:

a ventilation lumen between the ambience and a selected position above the carina:

an inflatable cuff system connected to said ventilation lumen for sealing the annulus between said ventilation lumen and the inside of the trachea when said cuff is inflated;

a lumen located proximal to said ventilation lumen and substantially located on the anterior side of said ventilation lumen through the apex of the triangular shaped glottis to maximize the crossectional area of the interior of said lumen, wherein said lumen has a first end at the ambience and a second end positioned to remove fluid from the trachea above the cuff; and a sheath for enclosing said ventilation lumen and said lumen proximal to said ventilation lumen, wherein the crossection of said sheath perpendicular to said ventilation lumen is substantially triangular, and wherein the location of said lumen anterior of said ventilation lumen maximizes the crossectional area of the interior of said lumen while minimizing contact between said sheath and the glottis.

2. An intratracheal tube as recited in claim 1, further comprising a suction lumen proximal to said ventilation lumen and having a first end at the ambiance and having a second end for removing fluid from below said cuff.

3. An intratracheal tube as recited in claim 1, further comprising an irrigation lumen proximal to said ventilation lumen and having a first end at the ambience and having a second end above said cuff for injecting a fluid in the trachea above said cuff.

4. An intratracheal tube as recited in claim 1, further comprising a catheter inserted through said lumen located proximal to said ventilation lumen for selectively transporting fluids.

5. An intratracheal tube as recited in claim 1, wherein the corners of the crossectional view of said sheath are rounded for the purpose of minimizing the irritation of the glottis and trachea.

* * * * *